US008217074B2

(12) United States Patent
Kim et al.

(10) Patent No.: US 8,217,074 B2
(45) Date of Patent: Jul. 10, 2012

(54) USE OF SARGACHROMENOL

(75) Inventors: Tae-Yoon Kim, Seoul (KR); Jong Heon Shin, Daejeon (KR); Bong Ho Lee, Daejeon (KR)

(73) Assignee: Catholic University Industry Academic Cooperation Foundation, Seoul (KR)

( * ) Notice: Subject to any disclaimer, the term of this patent is extended or adjusted under 35 U.S.C. 154(b) by 81 days.

(21) Appl. No.: 12/665,496

(22) PCT Filed: Aug. 7, 2007

(86) PCT No.: PCT/KR2007/003797
§ 371 (c)(1),
(2), (4) Date: Dec. 18, 2009

(87) PCT Pub. No.: WO2009/001979
PCT Pub. Date: Dec. 31, 2008

(65) Prior Publication Data
US 2010/0168222 A1 Jul. 1, 2010

(30) Foreign Application Priority Data
Jun. 22, 2007 (KR) .................. 10-2007-0061850

(51) Int. Cl.
*A01N 43/02* (2006.01)
*A61K 36/00* (2006.01)
(52) U.S. Cl. ................... 514/449; 424/725
(58) Field of Classification Search .................. None
See application file for complete search history.

(56) References Cited

U.S. PATENT DOCUMENTS
7,371,413 B2    5/2008   Simon et al.

OTHER PUBLICATIONS

Hur et al., "Sarquinoic acid and Sargachromenol, extract of Sagassum samiamu, induce apoptosis in HaCaT cells and mice skin: its potentiation of UVB-treated apoptosis", Annual Meeting of The Society of Investigative Dermatology, Journal of Investigative Dermatology, May 9, 2007, vol. 127, Issue S1, S138, Abstract presentation No. 825.*
Hur et al., "Sarquinoic acid and Sargachromenol, extract of Sagassum samiamu, induce apoptosis in HaCaT cells and mice skin: its potentiation of UVB-treated apoptosis", Annual Meeting of The Society of Investigative Dermatology, Journal of Investigative Dermatology, May 9, 2007, vol. 127, Issue S1, S138, Abstract presentation No. 825 (of record).*
Borzack, UV Rays, Sunblock and You!, available at http://healthy-lifestyle.most-effective-solution.com/2007/04/13/uv-rays-sunblock-and-you/, last visited Nov. 10, 2011.*
A.R. Haake, et al., 'Apoptosis: A Role in Skin Aging?', "The Journal of Investigative Dermatology", Symposium Proceedings, In Vitro Differentiated Melanocytes, Aug. 1998, vol. 3, No. 1., pp. 28-35, The Society for Investigative Dermatology, Inc., New York, USA.
E. Holzle, 'Pigmented Lesions As A Sign of Photdamage', "British Journal of Dermatology", 1992, 127, Supplement 41, pp. 48-50, Wiley-Blackwell.
S. Hur et al. "Sargaquinoic Acid and Sargachomenol, Journal of Investigative Dermatology" (2007), "Journal of Investigative Determatology", Abstract Presentation No. 825, vol. 127, Issue S1, S138, The Society for Investigative Dermatology.
Andrew Pawlowski, et al., 'Effects of UV Radiation on the Ultrastructure of Human Common Pigmented Naevi and Lentigines', "Acta-Dermato-Venereologica", vol. 71, No. 2, 1991, pp. 113-117, Society for the Publication of ActaDermato-Venereologica.
A.L.Perez-Castorena, et al., 'Evaluation of the Anti-Inflammatory and Antioxidant Activities of the Plastoquinone D Erivatives Isolated From Roldana Barba-Johannis', "Planta Med" 2002; vol. 68: No. 7, pp. 645-647, Georg Thieme Verlag.
Martin C. Raff, 'Social Controls on Cell Survival and Cell Death', "Nature", vol. 356, Apr. 2, 1992, pp. 397-400, Nature Publishing Group.
C, K Tsang, et al., 'Sargachromenol, A Novel Nerve Growth Factor-Potentiating Substance Isolated From *Sargassum macrocarpum*, Promotes Neurite Outgrowth and Survival Via Distinct Signaling Pathways in PC12D Cells', "Neuroscience" 132, (2005), pp. 633-643, Elsevier Ltd. on behalf of IBRO.
Hans Christian Wulf, et al., 'Skin Aging and Natural Photoprotection', "Micron" 35 (2004) pp. 185-191, Elsevier Ltd.
Antony R. Young, 'Acute Effects of UVR on Human Eyes and Skin', "Progress in Biophysics and Molecular Biology" 92 (2006), pp. 80-85, Elsevier Ltd.
Youngwan Seo, et al., 'Peroxynitrite-Scavenging Constituents From the Brown Alga *Sargassum thunbergii*', "Biotechnology and Bioprocess Engineering", 2004, vol. 9, No. 3: pp. 212-216. The Korean Society for Biotechnology and Bioengineering.

* cited by examiner

*Primary Examiner* — Sreeni Padmanabhan
*Assistant Examiner* — Svetlana M Ivanova
(74) *Attorney, Agent, or Firm* — Duane Morris LLP

(57) ABSTRACT

The present invention relates to novel use of sargachromenol, and more particularly, the present invention relates to novel use of sargachromenol for destroying and/or lysing hyperproliferating keratinocyte. Accordingly, since sargachromenol of the present invention has activity in destroying and/or lysing keratinocyte, it may be useful for keratinocyte lysing agents in the skin area where the keratinocytes are hyperproliferating or peeling agents.

3 Claims, 5 Drawing Sheets a c b

USE OF SARGACHROMENOL

TECHNICAL FIELD

The present invention relates to a novel use of sargachromenol, more particularly to a novel use of sargachromenol for destroying and/or lysing hyperproliferating keratinocytes.

BACKGROUND ART

The present invention relates to a novel use of sargachromenol, more particularly to a method for destroying and/or lysing keratinocytes using sargachromenol, a use for preparing an agent for lysing keratinocytes, and a composition for lysing keratinocytes.

Skin disease is caused by a variety of reasons. Because the skin, which is located at the outermost part of our body and covers the surface thereof, is always exposed to outside, skin disease may be caused by various skin irritating factors and pathogens. Further, it may be induced by hereditary factors, inflammations, benign or malignant tumors, hormones, injuries, or pathological changes such as retroplasia. Especially, damage to the stratum corneum, which is the outermost layer of the skin, may be a direct cause of skin disease.

When keratinocytes in the stratum basale of the epidermis divide through cell division, newly formed cells go upward to the outermost layer of the skin. There, the cells lose nuclei, become cornified and fall off the skin. This is called the turnover of the epidermis. That is, our skin is not maintained as it is after formed once, but is continually generated and lost. However, when the keratinocyte cell cycle is out of order because of genetic abnormalities, immunological abnormalities, infections by pathogens or mechanical or physical stimulations, a large number of problems may occur. Most skin diseases are caused by such reasons.

Apoptosis is a programmed cell death and may occur under several physiological and pathological situations. In normal cell tissues, cell proliferation and apoptosis are balanced and the number of cells in the tissue is maintained constant. However, in cancer or tumor cell tissues, the number of cells increases dynamically because apoptosis does not match the rapid cell proliferation [Raff. M. C., *Nature*, 356:397. 1992]. Accordingly, control of apoptosis may be a solution to the prevention or improvement of skin disease caused by hyperproliferation of keratinocytes.

Typical examples of skin disease caused by the hyperproliferation of keratinocytes include skin aging, photoaging and pigmentary diseases. Skin aging and photoaging are caused by external factors such as chronic exposure to UV associated with generation of oxygen free radicals inside the body, which result in peroxidation of the lipid components of the cell membrane and hardening of the cell membrane, thereby interfering with the supply of oxygen and nutrients into cells. As skin metabolism and replacement of skin cells are retarded because of the reasons, the stratum corneum of the skin becomes thicker and the skin experiences a lot of changes in structure and function. As a result, series of skin aging and photoaging are occurred, appearing many characteristics such as skin aging, loss of elasticity, wrinkle formation, decline of moisture holding capacity, droop and the like [Wulf H C. et al., *Micron*. 2004, 35, 185-91; Haake A R, et al., *J. Investigative Dermatol. Symp. Proc.* 1998, 3, 28-35]. In addition, pigmentation occurs, such as chloasma, dark spots, and the like [Young A R. *Prog. Biophys. Mol. Biol.* 2006, 92(1), 80-5, HE. *Br. J. Dermatol.* 1992, 127 Suppl. 41:48-50, Pawlowski A et al., *Acta Derm. Venereol.* 1991, 71(2), 113-7].

Accordingly, destroying of keratinocytes in thickened cells is effective in preventing these symptoms.

Mechanical or chemical peeling is carried out to remove keratinocytes. However, chemical peeling tends to induce irritations, inflammations, and the like. For example, chemical peeling agents such as lactic acid, glycolic acid, etc. have been used to remove fine wrinkles through facilitated removal of the horny layer. But, their use is restricted because they may cause skin irritation at specific concentration or pH. Accordingly, development of an improved agent for removing keratinocytes without skin side effects such as irritations, inflammations, and the like is needed.

In the present description, several literatures and patent publications are cited. They are specified in parentheses. The disclosure of the cited literatures and patent publications is enclosed in the present description in its entirety, and serves to describe the technical field to which the present invention belongs and the contents of the present invention more clearly.

[Disclosure]

The inventors of the present invention have been working on materials having keratinocyte removing and/or lysing activity and with little skin irritation or other side effect. As a result, we isolated and purified sargachromenol from naturally growing *Sargassum sagamianum*, and found out, for the first time, that the sargachromenol of the present invention exhibits a remarkable activity of inducing apoptosis of keratinocytes.

Accordingly, in an aspect, the present invention provides a method for destroying and/or lysing skin keratinocytes comprising applying sargachromenol represented by the following Chemical Formula I on the skin area where keratinocytes are hyperproliferating:

<Chemical Formula I>

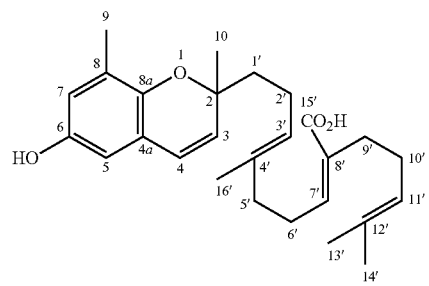

In another aspect, the present invention provides a use of the sargachromenol represented by Chemical Formula I for preparing a keratinocyte lysing agent.

In still another aspect, the present invention provides a composition for lysing keratinocytes comprising the sargachromenol represented by Chemical Formula I and a dermatologically acceptable vehicle.

The above and other aspect, objects, features and other advantages of the present invention will be more clearly understood from the following detailed description when taken in conjunction with the accompanying drawings and claims.

Best Mode

Hereunder is given a more detailed description of the present invention.

The sargachromenol of the present invention can be represented by the following Chemical Formula I.

<Chemical Formula I>

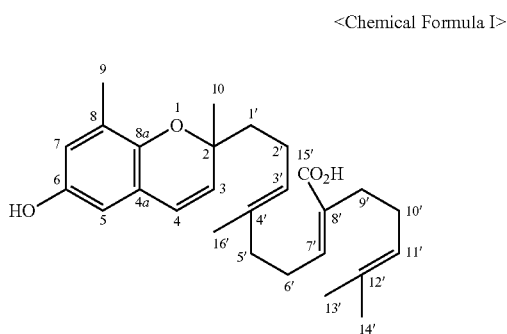

The sargachromenol of the present invention can be obtained and isolated from the nature. That is, it can be obtained from plant using the conventional method for extracting and isolating substances. The extract can be obtained by extracting using an adequate organic solvent after drying and maceration or after drying only. The resultant extract can be purified by a purification method well known to those skilled in the art to which the present invention belongs. Preferably, the sargachromenol of the present invention may be obtained and isolated from *Sargassum sagamianum*.

*Sargassum sagamianum* is a seaweed belonging to the family Sargassaceae and is distributed along the eastern and southern coasts of Korea and the coasts of Japan. Sargachromenol extracted from *Sargassum sagamianum* is reported to have NGF (nerve growth factor)-dependent nerve cell growth promoting activity [Chi Kwan Tsang et al, *Neuroscience*, 2005]. However, there is no report on skin disease prevention or improvement activity of sargachromenol.

For the isolation and the purification of the inventive sargachromenol, first of all, an extract was prepared from *Sargassum sagamianum* by using water or C1-C6 organic solvent. The said organic solvent may be methanol, ethanol, propanol, isopropanol, butanol, acetone, ether, benzene, chloroform, ethyl acetate, methylene chloride, hexane, cyclohexane, petroleum ether alone or mixed together. Preferably, it may be methanol, and most preferably it may be chloroform or ethyl acetate. The said methanol extract was performed column chromatography using column filled with synthetic resin such as silica gel or activated alumina and TLC alone or together, and as a result, sargaquinoic acid was isolated. Preferably, silica gel column chromatography and octadecyl silica gel column chromatography may be used in parallel. The extract was prepared from the said sargaquinoic acid by using alcohol and chloroform solvent. The said alcohol may be methanol, ethanol, propanol, isopropanol, butanol and the like and it may be used alone or mixed together. Preferably, mixture of chloroform and methanol may be used. From the said extract, the isolation and the purification of the inventive sargachromenol can be performed by using the TLC for silica fractionation. However, the method for the isolation and the purification of the effective component are not limited to the above described (FIG. 1)

The sargachromenol of the present invention induces cytotoxicity and apoptosis of keratinocytes, thereby destroying and/or lysing keratinocytes at the skin area where the keratinocytes are hyperproliferating.

The sargachromenol of the present invention has cytotoxic effect on keratinocytes at the skin area where the keratinocytes are hyperproliferating. The keratinocytes hyperproliferate at the aged, photoaged or pigmented skin. Although not limited thereto, the pigmented skin refers to the skin where chloasma or dark spots are formed. In the examples that follow, cytotoxic effect on human keratinocytes treated by the sargachromenol of the present invention was confirmed through MTT analysis. The cytotoxic effect was concentration-dependent (see FIG. 2a).

Further, the sargachromenol of the present invention induces apoptosis of keratinocytes. In the examples that follow, inducement of apoptosis of human keratinocytes treated with sargachromenol was investigated through FACS and TUNEL analysis. Apoptosis effect was significantly higher than the human keratinocytes not treated by sargachromenol. The apoptosis effect increased as sargachromenol concentration and treatment time increased (see FIGS. 2b and 2c).

The sargachromenol of the present invention induces cell apoptosis by activating apoptosis-related factors. When human keratinocytes were treated with the sargachromenol of the present invention and activities of apoptosis-related factors were investigated, it was observed that caspase-8 and caspase-3 were cleaved by activation. Further, it was confirmed that the activities of apoptosis-related factors increased further when the concentration of the sargachromenol of the present invention was higher (see FIG. 3).

Cell apoptosis can be further promoted by, irradiating UV, in addition to treatment with sargachromenol.

In the examples that follow, apoptosis effect was investigated after treating human keratinocytes with sargachromenol followed by irradiation of UVB. Apoptosis effect was remarkably improved when the cells were irradiated with UV (see FIG. 4), and activities of apoptosis-related factors also increased further when UV was irradiated (see FIG. 5).

Accordingly, the present invention provides a method for destroying and/or lysing skin keratinocytes at the skin area where the keratinocytes are hyperproliferating, which is accomplished as the sargachromenol of the present invention induces cytotoxicity and apoptosis of skin keratinocytes by activating apoptosis-related factors. Further, the activity of destroying and/or lysing keratinocytes of the sargachromenol of the present invention is enhanced by irradiation of UV. Skin keratinocytes hyperproliferate because of skin aging, photoaging and pigmentation, resulting in, although not limited thereto, aged skin, wrinkles, chloasma and dark spots caused by UV in skin. Accordingly, the sargachromenol of the present invention, which has the activity of destroying and/or lysing keratinocytes, can be effectively used as keratinocyte lysing agent at the skin area where keratinocytes are hyperproliferating because of aging, photoaging and pigmentation. The keratinocyte lysing agent may also be used for skin peeling.

The present invention further provides a use of the sargachromenol represented by Chemical Formula I for the preparation of a keratinocyte lysing agent.

The present invention further provides a composition for lysing keratinocytes comprising the sargachromenol represented by Chemical Formula I and a dermatologically acceptable vehicle.

Keratinocytes, which account for over 95% of epidermal cells, produce the protein keratin and differentiate into basal cells, prickle cells and granular cells. Through turnover cycle, skin is continually generated and lost. But, when skin becomes aged or aged cells remain in the skin, the stratum corneum of the skin becomes thicker, resulting in skin disease such as wrinkles, chloasma, dark spots and the like.

A composition for lysing keratinocyte of this invention contains sargachromenol as an effective component, and may comprise a dermatologically acceptable vehicle and be prepared in the form of base makeup product (skin toner, cream, essence, face cleansing compositions such as cleansing foam, and cleansing water, pack, body oil), coloring cosmetics (foundation, lip stick, mascara, makeup base), haircare products (shampoo, rinse, hair conditioner, hair gel) and soap. As used herein, the term "dermatologically acceptable" refers to physiologically acceptable and when applied onto the skin or administered, generally does not cause allergic reactions or similar reactions thereto.

The vehicle of this invention may comprise, but not limited thereto, skin softener, skin infiltration enhancer, colorant, odorant, emulsifier, thickener, and solvent. In addition, it may comprise supplementary flavor, pigment, disinfectant, antioxidant, preservative, and humectant, and to improve physical property, it may comprise thickening agent, inorganic salts, synthetic polymers. For example, in case of manufacturing a face cleansing composition and a soap which containing sargachromenol of this invention, it may be easily prepared by adding sargachromenol to conventional cleansing composition or soap base. In case of manufacturing cream, it may be prepared by adding sargachromenol or the salt thereof to general oil-in-water cream base. In addition, it may comprise flavor, chelating agent, pigment, antioxidant, preservative and to improve physical property, it may comprise synthetic or natural materials such as protein, minerals, vitamins. In addition, composition for lysing keratinocyte of this invention may be prepared in the form of skin peeling reagent for chemical peeling.

The amount of sargachromenol in the composition for lysing keratinocyte of this invention may be 0.0001 to 50 w/w %, preferably 0.01 to 10 w/w %.

Hereinafter, the present invention will be described in detail by examples. It is to be understood well, however, that these examples are for illustrative purpose only and are not constructed to limit the scope of the present invention.

MODE FOR INVENTION

Figure 1:
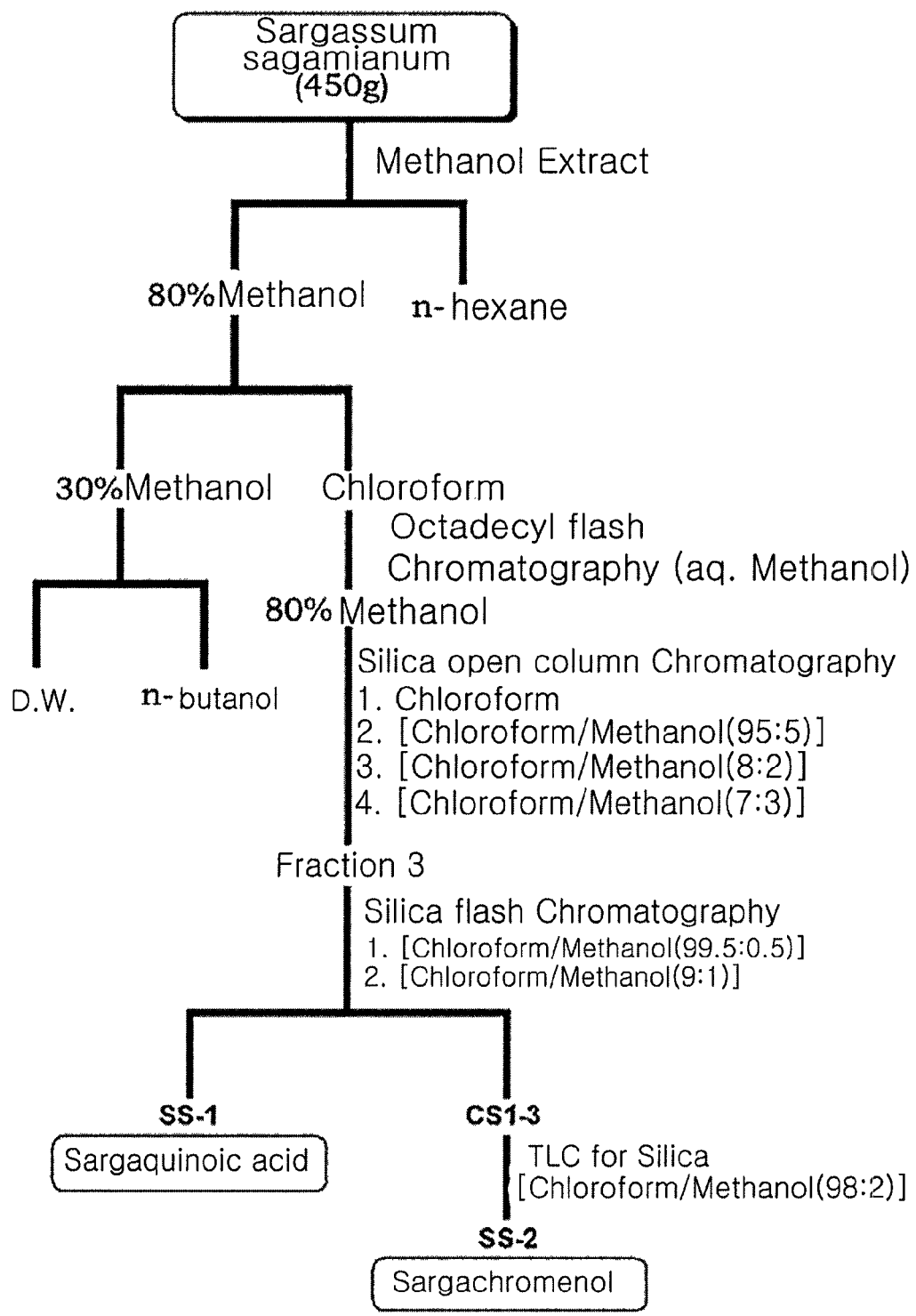
FIG. 1 is a scheme of extracting process of sargachromenol from *Sargassum sagamianum*

Hereinafter, the present invention will be described in detail by examples. However, that these examples are not limit the scope of the present invention.

EXAMPLE 1

Extraction and Isolation of Sargachromenol 450 g of *Sargassum sagamianum* (obtained in Seongsan, Jeju) was powdered by a grinder, and then repeatedly extracted with 4 L of 100% methanol at room temperature for 24 hours, for 3 times. The extract was concentrated using a rotary evaporator (Buchi). About 38 g of methanol extract was obtained. All the 38 g of methanol extract was dissolved in 80% methanol and subjected to solvent fractionation using n-hexane to remove nonpolar materials. The remaining active fraction of the 80% methanol layer was further fractionated into a 30% methanol layer and a chloroform layer. The 30% methanol layer was further fractionated using water and n-butanol. The chloroform layer was subjected to octadecyl silica flash chromatography using methanol solvent, and then 12 g of 80% methanol fraction was obtained. About 2 g of the 80% methanol fraction was subjected to silica column chromatography, using 100% chloroform and mixture solvents of chloroform and methanol (95:5, 8:2 and 7:3) as eluent. Five fractions were obtained. 445 mg of the third fraction among them was subjected to silica flash chromatography using 99.5:0.5 mixture solvent of chloroform and methanol as eluent. Then, silica flash chromatography was carried out again, using 9:1 mixture solvent of chloroform and methanol as eluent. 187 mg of sargaquinoic acid was obtained. Then, TLC for silica fractionation was carried out using 98:2 mixture solvent of chloroform and methanol. 37 mg of pure sargachromenol was obtained.

EXAMPLE 2

Investigation of Cytotoxicity of Sargachromenol 2-1. Cytotoxicity Analysis by MTT Assay Cytotoxicity effect of the sargachromenol of the present invention isolated and purified in Example 1 on human keratinocytes HaCaT was investigated by MTT cell viability analysis.

HaCaT cells were obtained from Professor N. Fusenig of the German Cancer Research Institute. The HaCaT cells were incubated in DMEM medium containing 10% FBS (Hyclone), 100 unit/mL penicillin and 100 µg/mL streptomycin at 37° C., in a 5% $CO_2$ incubator. During the incubation, cell viability and number of cells were measured periodically using a hemacytometer (Neubauer, Germany) by the trypan blue exclusion method. In all experiments, initial cell viability was maintained over 95%.

The cultured HaCaT cells were transferred to a 96-well plate, with $5 \times 10^4$ cells/well, and incubated at 37° C. in a 5% $CO_2$ incubator for 24 hours. Then, the cultured HaCaT cells were treated with 0, 1, 2, 5 or 10 µg/mL sargachromenol, and further incubated at 37° C. in a 5% $CO_2$ incubator for 24 hours. Then, without removing the medium, each well was treated with 5 mg/mL MTT reagent at a concentration of 20 µL/100 µL, and incubated for 2 hours. Subsequently, after removing the medium, 150 µL of DMSO was added to each well and cell viability was analyzed by measuring absorbance at 540 nm using an ELISA reader (Molecular Devices, USA). Cells non-treated with sargachromenol were used as control group. Cell viability was calculated as relative value of that of the control group (100%).

Figure 2:
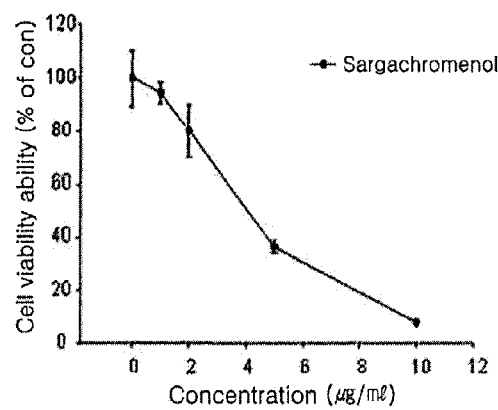
FIG. 2 is the results of (a) MTT assay, (b) FACS assay, (c) TUNEL assay showing cytotoxic effect of sargachromenol in human keratinocytes.
Figure 2:
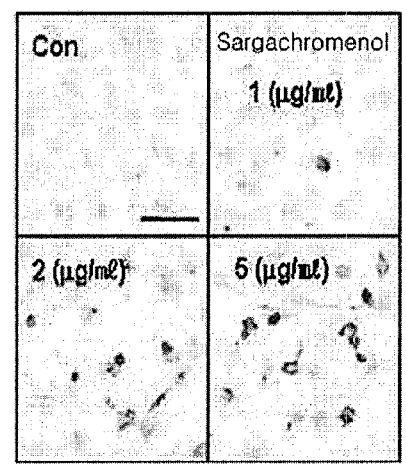
Figure 2:
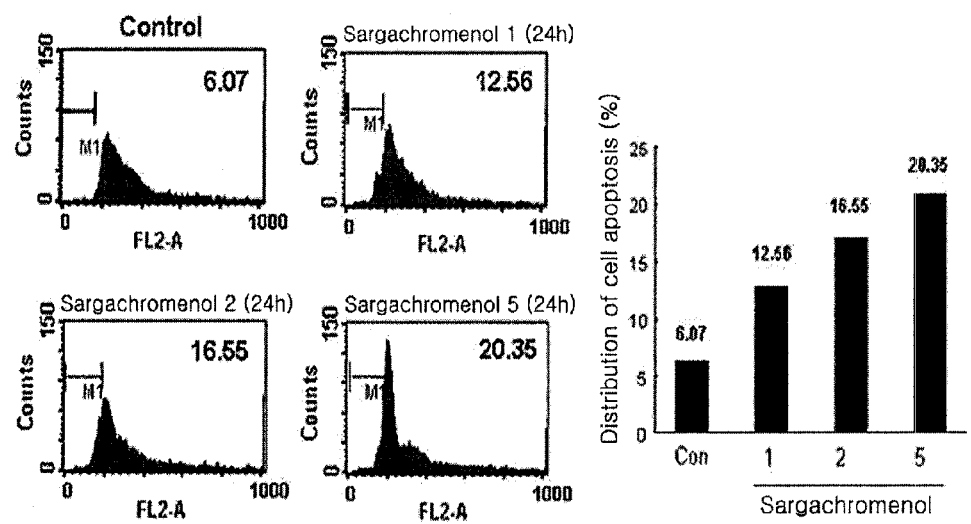

As a result, cell viability decreased as the concentration of sargachromenol increased. The cell viability was reduced by 40% when the cells were treated with 5 µg/mL sargachromenol (FIG. 2a). Accordingly, it was confirmed that the sargachromenol of the present invention has toxic effect on human keratinocytes.

2-2. Cytotoxicity Measurement by FACS and TUNEL (TdT-mediated dUTP Nick-end Labeling) Method Apoptosis effect of the sargachromenol of the present invention on human keratinocytes was investigated by FACS and TUNEL analysis. First, for FACS analysis, HaCaT cells were cultured in the same manner as in Example 2-1, transferred to a 10 cm plate, with $2 \times 10^6$ cells/well, and incubated at 37° C. in a 5% $CO_2$ incubator for 24 hours. After treating the cells with 0, 1, 2 or 5 µg/mL sargachromenol, they were incubated at 37° C. in a 5% $CO_2$ incubator for 24 hours. Then, the cells were released from the plate using trypsin, and fixed using 4% paraformaldehyde. The fixed cells were treated with 70% alcohol to increase cell membrane permeability. Then, the cells were stained with Propidium Iodide (PI) solution for 30 minutes, and subjected to FACS analysis. Cells treated with DMSO only and not with sargachromenol were used as control group.

For TUNEL analysis, the cells were incubated for 24 hours as above, and transferred to a chamber slide using an ApopTag® fluorescein in situ apoptosis detection kit. After adhering the cells to the bottom well, they were washed with pH 7.4 PBS solution. The chamber slide was immersed in PBS solution of 4% paraformaldehyde for 30 minutes at room temperature in order to completely fix the cells. And, the cells were washed with PBS and immersed in blocking solution (1% $H_2O_2$ in methanol) for 30 minutes at room temperature in order to inhibit the action of endogenous peroxidase. Then, the cells were washed with PBS and immersed in 0.1% sodium citrate solution containing 0.1% Triton X-100 at 4° C. for 2 minutes in order to make the cells permeable. For labeling, the cells were washed with PBS two more times and diluted TUNEL reaction mixture was added to the slide. After incubating in a 37° C. humidified chamber for 60 minutes, the slide was washed with PBS. Then, the slide was further incubated in TBS solution containing 1% BSA and 5% FBS for 20 minutes. After adding anti-fluorescein antibody conjugated with horse-radish peroxidase to the culture medium and reacting at 37° C. for 1 hour, the slide was washed with PBS and DAB-matrix solution was added. Hematoxylin solution was added for counter staining. Then, the slide was washed with PBS and observed with a microscope after placing a glass coverslip on the slide. Dead, TUNEL-positive, cells were stained dark brown, whereas the counter-stained cells were blue.

As a result, it was confirmed through FACS analysis that apoptosis effect was superior in the cells treated with sargachromenol than in the control group. Apoptosis effect was better at treatment with 5 μg/mL than 1 μg/mL (FIG. 2b). As in FACS analysis, TUNEL analysis also confirmed that the number of TUNEL-positive cells, that is dead cells, increased as the concentration of the sargachromenol of the present invention increased (FIG. 2c). Accordingly, it was confirmed that the sargachromenol of the present invention has concentration-dependent cytotoxic effect on human keratinocytes.

EXAMPLE 3

Keratinocyte Destroying Effect of Sargachromenol

Human keratinocytes HaCaT cells were cultured in the same manner as in Example 2-1 and transferred to a 10 cm plate, at $2 \times 10^6$ cells/well. After about 18 hours of serum starvation, the cells were treated with 0, 1, 2 or 5 μg/mL sargachromenol. 18 hours later, the cells were lysed using RIPA buffer [12 mM EDTA, 137 mM NaCl, 20 mM Tris-HCl (pH 8.0), 1 mM $Na_3VO_4$ (Sigma-Aldrich, USA) 10 mM NaF (Sigma), 1 mM PMSF (Sigma), 1% Triton X-100, 10% glycerol and protease inhibitor cocktail (Roche, Germany)]. The lysed cells were put in a 1.5 mL tube and, after pipetting, put on ice for 20 minutes. The lysate was centrifuged at 14000 rpm for 20 minutes, and protein was isolated from the supernatant. Sample concentration of the isolated protein was determined using a BCA protein analysis kit (Pierce, Rockford, Ill.) and electrophoresis (SDS-PAGE) was carried out. Western blot analysis was carried out on the protein isolated by the electrophoresis. Western blot analysis was carried out as follows. After electrophoresis of the sample, the protein was transferred from the gel to a polyvinylidene fluoride membrane (Pall Corporation). Then, after blocking the membrane at room temperature for 2 hours using 3% BSA solution (Amresco, USA), it was treated with primary antibodies and reaction was carried out at room temperature for 2 hours. The primary antibodies were anti-caspase-3 antibody, anti-caspase-8 antibody and anti-actin antibody (Cell Signaling Technology, Beverly, Mass.), which are antibodies associated in apoptosis-related signaling. After reaction with the primary antibodies, it was washed with TBS for about 15 minutes and further reacted for 45 minutes by treating with secondary antibodies. The secondary antibodies were goat anti-mouse antibody and goat anti-rabbit antibody (Zymed, San Francisco, USA). Then, after washing sufficiently with TBS for over 30 minutes, protein was identified using an ECL detection kit (Santa Cruz). Cells not treated with sargachromenol were used as control group.

Figure 3:
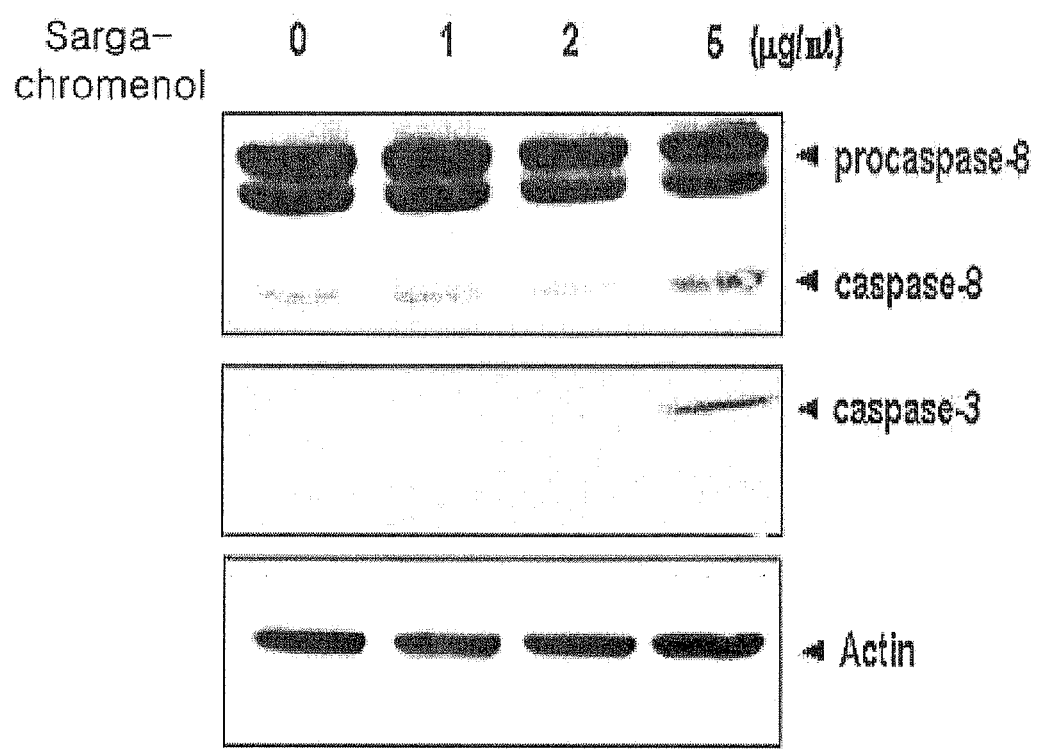
FIG. 3 is a western blot result which shows apoptotic effect of sargachromenol with dose-dependent in human keratinocytes.

As a result, it was identified that, 24 hours after the treatment with sargachromenol, caspase-8 and caspase-3 were cleaved by activation of apoptosis-inducing factors at higher concentration of sargachromenol. Further, it was confirmed that the quantity of cleaved protein also increased in a concentration-dependent manner (FIG. 3).

Thus, it was confirmed that the sargachromenol of the present invention has the activity of inducing apoptosis of human keratinocytes by specifically activating the apoptosis-related proteins caspase-8 and caspase-3.

EXAMPLE 4

Synergic Apoptosis Effect by UV and Sargachromenol

Synergic apoptosis effect by UV and sargachromenol on human keratinocytes was investigated. HaCaT cells were cultured in the same manner as in Example 2-1 and transferred to a 6-well plate, at $3 \times 10^5$ cells/well. After about 12 hours of serum starvation, each well was pre-treated with 0, 0.5, 1, 2, 5 or 10 μg/mL sargachromenol, and UVB was irradiated at 150 J/m² (FS24T12/UVB/HO, Voltare Co., Fairfield, Conn., USA, 290-320 nm). 18 hours later, without removing the medium, each well was treated with 5 mg/mL MTT reagent at a concentration of 20 μL/100 μL, and incubated for 2 hours. Subsequently, after removing the medium, 150 μL of DMSO was added to each well and cell viability was analyzed by measuring absorbance at 540 nm using a spectrophotometer. Cells non-treated with sargachromenol were used as control group. Cell viability was calculated as relative value of that of the control group (100%).

Figure 4:
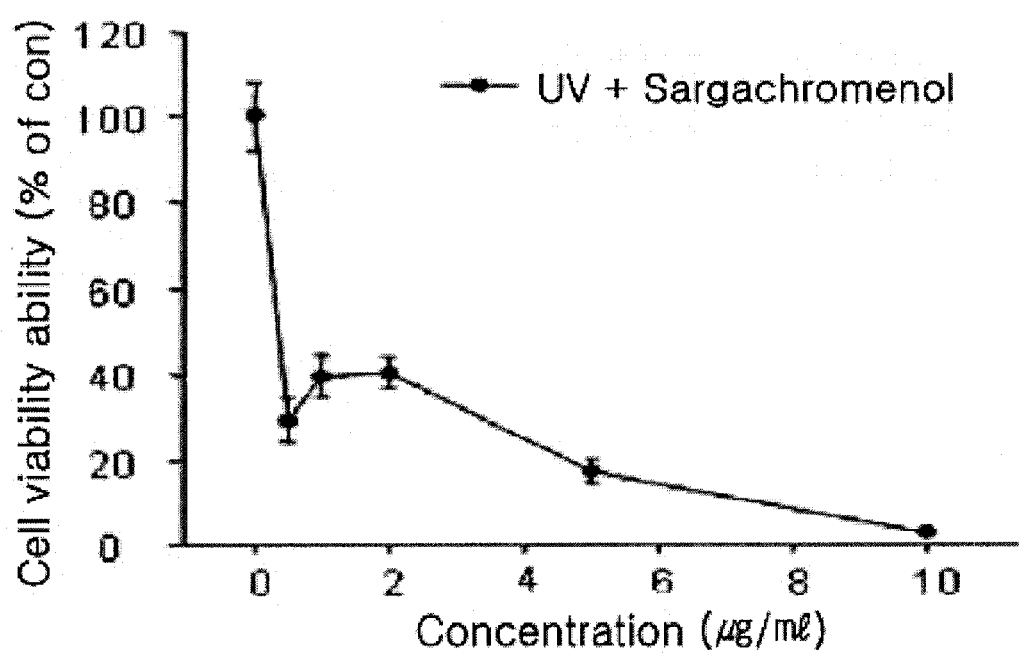
FIG. 4 is a MTT assay result which shows apoptotic effect of sargachromenol in UV B radiated human keratinocytes.

As a result, the cells pre-treated with sargachromenol and irradiated with UV exhibited much more increased apoptosis (FIG. 4) than the cells treated with sargachromenol under the same condition but without being radiated with UV (FIG. 2a). Especially, whereas the cells treated with sargachromenol only without UV irradiation showed cell viability of not less than 40% at the sargachromenol concentration of 5 μg/mL, the cells pre-treated with sargachromenol and irradiated with UV showed cell viability of only about 25% even at a lower sargachromenol concentration of 1 μg/mL. Accordingly, it was confirmed that UV outstandingly enhances the apoptosis effect of sargachromenol.

EXAMPLE 5

Effect of UV on Sargachromenol-induced Apoptosis-related Factors

In Example 4, it was confirmed that UV further enhances the apoptosis of human keratinocytes by sargachromenol.

Thus, it was investigated whether UV has effect on sargachromenol-induced apoptosis-related factors. First, human keratinocytes HaCaT cells were cultured in the same manner as in Example 2-1 and transferred to a 10 cm plate, at $2\times10^6$ cells/well. After about 18 hours of serum starvation, each well was pre-treated with 0, 2 or 5 10 μg/mL sargachromenol for 30 minutes and UVB was irradiated. 8 hours later, the cells were lysed using RIPA buffer [12 mM EDTA, 137 mM NaCl, 20 mM Tris-HCl (pH 8.0), 1 mM $Na_3VO_4$ (Sigma-Aldrich, USA) 10 mM NaF (Sigma), 1 mM PMSF (Sigma), 1% Triton X-100, 10% glycerol and protease inhibitor cocktail (Roche, Germany)]. Electrophoresis (SDS-PAGE) was carried out after determination of protein concentration. Western blot analysis was carried out on the isolated protein as in Example 3. Cells not treated with sargachromenol were used as control group.

Figure 5:
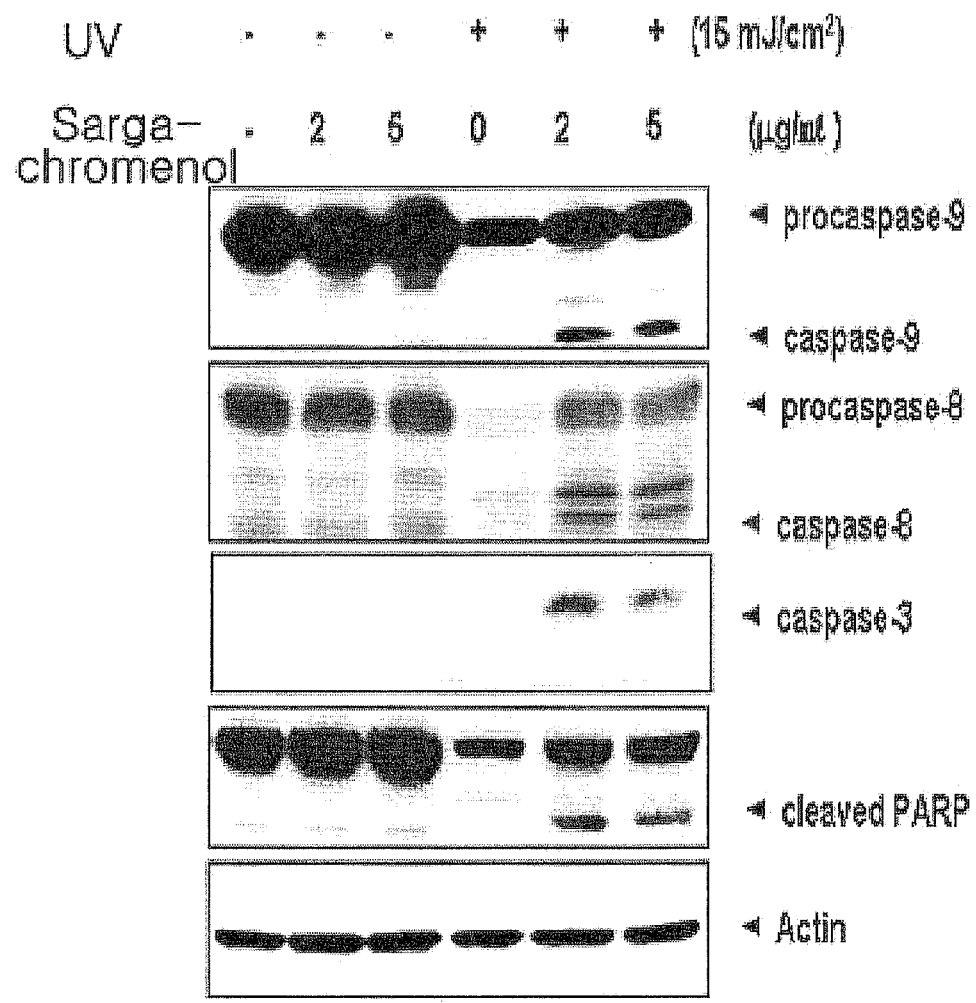
FIG. 5 is a western blot result which shows effect of sargachromenol in expression of apoptosis related factors in UV B radiated human keratinocytes.

As a result, when the cells were pre-treated with sargachromenol and irradiated with UVB, cleaved caspase-8, caspase-9 and caspase-3 were observed 8 hour later. In contrast, when the cells were treated with 2 or 5 μg/mL sargachromenol only, activation of caspase was not observed (FIG. 5). Activation of caspase was observed 18 hours later when the cells were treated with 5 μg/mL sargachromenol only (FIG. 3). Thus, it was confirmed that the apoptosis induced by sargachromenol can be advanced by UV treatment. In addition, activation of caspase was observed in the cells not treated with sargachromenol but treated with UV only (FIG. 5).

From the experimental results, it was confirmed that apoptosis-related factors such as caspase-8, caspase-9, caspase-3, PARP, etc. are further activated when human keratinocytes are treated with sargachromenol along with UVB than when they are treated with sargachromenol alone. Thus, the combination of the two was confirmed to induce apoptosis of keratinocytes remarkably. Accordingly, when the sargachromenol of the present invention is treated in combination with UV, therapeutic effect on skin disease would be enhanced through more effective apoptosis of keratinocytes.

PREPARATION EXAMPLES

Preparation of Agent for Removing Keratinocytes Comprising Sargachromenol of the Present Invention Preparation Example 1

Preparation of Cream 40 g of a cream base comprising an oil component, an aqueous component, a surfactant, and the like, e.g., comprising 1.5 g of stearic acid, 2.2 g of stearyl alcohol, 0.5 g of butyl stearate, 0.5 g of propylene glycol, 2.0 g of glycerin monostearate and 0.3 g of potassium hydroxide, was mixed with 0.1% (w/w) sargachromenol of the present invention. After emulsifying well in a mixer, a cream composition was prepared through degassing, filtration and cooling. A chelating agent, a fragrance and a pigment were added to the composition as additives. An oil-in-water type composition containing a small amount of oil component was prepared.

Preparation Example 2

Preparation of Skin Softener

Skin softener comprising sargachromenol was prepared as in the following Table 1. An aqueous component was added to purified water and dissolved at room temperature to prepare an aqueous phase. Sargachromenol, an oil component, an emulsifier, an antiseptic and a fragrance were dissolved at room temperature, added to and mixed with the aqueous phase, and filtered.

TABLE 1

Skin softener comprising sargachromenol

| Components | Contents (weight %) |
|---|---|
| Sargachromenol | 0.1 |
| EDTA | 0.05 |
| PEG 1500 | 4.00 |
| Carbomer | 0.16 |
| 1,3-Butylene glycol | 3.00 |
| Polyoxyethylene hydrogenated castor oil | 0.45 |
| Triethanolamine | 0.12 |
| Antiseptic, fragrance and pigment | negligible |
| Purified water | residual |
| Total | 100 |

Preparation Example 3

Preparation of Astringent

Astringent comprising sargachromenol was prepared as in the following Table 2. An aqueous component was added to purified water and dissolved at room temperature to prepare an aqueous phase. Sargachromenol, an oil component, an emulsifier, an antiseptic and a fragrance were dissolved in ethanol at room temperature to prepare an alcohol phase, which was added to and mixed with the aqueous phase, and filtered.

TABLE 2

Astringent comprising sargachromenol

| Components | Contents (weight %) |
|---|---|
| Sargachromenol | 0.1 |
| Glycerin | 2.00 |
| 1,3-Butylene glycol | 3.00 |
| EDTA | 0.05 |
| Ethanol | 7.00 |
| Polyoxyethylene hydrogenated castor oil | 0.40 |
| Antiseptic, fragrance and pigment | negligible |
| Purified water | residual |
| Total | 100 |

Preparation Example 4

Preparation of Lotion

Lotion comprising sargachromenol was prepared as in the following Table 3. An aqueous phase comprising purified water, triethanolamine and butylene glycol was dissolved by heating at 70° C. Then, an oil phase comprising a fatty acid, an oil component, an emulsifier and an antiseptic dissolved by heating at 70° C. was added. After emulsification was completed, 2% xanthan gum solution, a hydrophilic thickening agent, was added at a concentration of 0.05 weight % based on the total weight. After cooling the solution to 45° C., sargachromenol, a fragrance and a pigment were added and cooled to 30° C. after mixing.

TABLE 3

Lotion comprising sargachromenol

| Components | Contents (weight %) |
|---|---|
| Sargachromenol | 0.1 |
| Glycerin | 3.00 |
| Carbomer | 0.10 |
| Xanthan gum | 0.05 |
| 1,3-Butylene glycol | 3.00 |
| Polyglycerin-3-methylglucose distearate | 1.50 |
| Glycerin distearate | 0.50 |
| Cetearyl alcohol | 0.30 |
| Jojoba oil | 3.00 |
| Liquid paraffin | 2.00 |
| Squalane | 3.00 |
| Dimethicone | 0.50 |
| Tocopheryl acetate | 0.20 |
| Triethanolamine | 0.10 |
| Antiseptic, fragrance and pigment | negligible |
| Purified water | residual |
| Total | 100 |

Preparation Example 5

Preparation of Gel

Gel comprising sargachromenol was prepared as in the following Table 4.

TABLE 4

Gel comprising sargachromenol

| Components | Contents (weight %) |
|---|---|
| Sargachromenol | 0.1 |
| EDTA | 0.02 |
| 1,3-Butylene glycol | 4.00 |
| Carbomer | 0.60 |
| Glycerin | 5.00 |
| Hydroxyethyl cellulose | 0.15 |
| Triethanolamine | 0.50 |
| Triclosan | 0.20 |
| Ethanol | 5.00 |
| Polyoxyethylene hydrogenated castor oil | 4.00 |
| Antiseptic, fragrance and pigment | negligible |
| Purified water | residual |
| Total | 100 |

Preparation Example 6

Preparation of Essence

Essence comprising sargachromenol was prepared as in the following Table 5. A thickening agent was uniformly dispersed in purified water by slowly adding while stirring. Aqueous components were mixed to prepare an aqueous phase. An emulsifier, a skin emollient, a fragrance and an antiseptic were dissolved in ethanol. The resultant alcohol phase was added to the aqueous phase while stirring, and an alkali agent was added. Finally, sargachromenol and a pigment were added.

TABLE 5

Essence comprising sargachromenol

| Components | Contents (weight %) |
|---|---|
| Sargachromenol | 0.1 |
| EDTA | 0.05 |
| Potassium cetyl phosphate | 0.30 |
| Glycerin | 5.00 |
| 1,3-Butylene glycol | 4.00 |
| Glyceryl stearate/PEG-100 stearate | 0.50 |
| Sorbitan stearate | 0.30 |
| Jojoba oil | 0.50 |
| Macadamia nut oil | 0.50 |
| Tocopheryl acetate | 0.50 |
| Butylated hydroxytoluene | 0.05 |
| Dimethicone | 3.00 |
| Polyacrylamide/$C_{13}$-$C_{14}$ isoparaffin/laureth 7 | 1.50 |
| Glyceryl polymethacrylate/propylene glycol | 5.00 |
| Ethanol | 3.00 |
| Antiseptic, fragrance and pigment | negligible |
| Purified water | residual |
| Total | 100 |

[Industrial Applicability]

Since sargachromenol of this invention has ability of destroying and/or lysing hyperproliferating keratinocytes, it may be used as keratinocytes lysing agent or peeling agent for skin which is hyperproliferated with keratinocytes by aging, photoaging or pigmentation.

This application claims priority to Korean Patent Application No. 10-2007-61850, filed on Jun. 22, 2007, the contents of which are hereby incorporated by reference.

As mentioned above, the present invention was described in detail. However, these description was one of preferable embodiments and it is certain that it is not limit the scope of the present invention. Accordingly, substantive scope of this invention is referred by attached claims and their equivalents.

The invention claimed is:

1. A method of destroying and/or lysing skin keratinocytes comprising applying sargachromenol represented by Chemical Formula I on a skin area where the keratinocytes are hyperproliferating

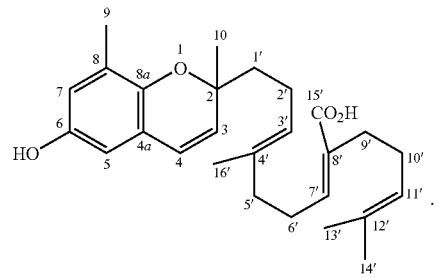

<Chemical Formula I>

2. The method according to claim 1, wherein the skin area where the keratinocytes are hyperproliferating is selected from the group consisting of aged skin, photoaged skin, and pigmented skin.

3. The method according to claim 2, wherein the pigmented skin is the skin where chloasma or dark spots are formed.

* * * * *